(12) United States Patent
Heikenfeld

(10) Patent No.: US 11,627,893 B2
(45) Date of Patent: Apr. 18, 2023

(54) SKIN PRODUCT SWEAT TESTING DEVICES AND METHODS

(71) Applicant: University of Cincinnati, Cincinnati, OH (US)

(72) Inventor: Jason C. Heikenfeld, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 408 days.

(21) Appl. No.: 16/637,541

(22) PCT Filed: Aug. 10, 2018

(86) PCT No.: PCT/US2018/046215
§ 371 (c)(1),
(2) Date: Feb. 7, 2020

(87) PCT Pub. No.: WO2019/032965
PCT Pub. Date: Feb. 14, 2019

(65) Prior Publication Data
US 2020/0253512 A1    Aug. 13, 2020

Related U.S. Application Data

(60) Provisional application No. 62/543,429, filed on Aug. 10, 2017.

(51) Int. Cl.
*A61B 5/145*    (2006.01)
*A61B 5/0531*    (2021.01)
(Continued)

(52) U.S. Cl.
CPC ........ *A61B 5/14521* (2013.01); *A61B 5/0531* (2013.01); *A61B 5/6832* (2013.01);
(Continued)

(58) Field of Classification Search
CPC .. A61N 1/0448; A61N 1/0476; A61N 1/0484; A61N 1/0496; A61N 1/30;
(Continued)

(56) References Cited

U.S. PATENT DOCUMENTS

2015/0112164 A1    4/2015    Heikenfeld et al.
2015/0112165 A1    4/2015    Heikenfeld

FOREIGN PATENT DOCUMENTS

WO    2016138087 A1    9/2016

OTHER PUBLICATIONS

Search Report and Written Opinion in International Patent Application No. PCT/US2018/046215, dated Dec. 4, 2018, 11 pgs.

*Primary Examiner* — Brian T Gedeon
(74) *Attorney, Agent, or Firm* — Wood Herron & Evans LLP

(57) ABSTRACT

Described are methods and devices (100) for measuring a sweat property of skin (12) in response to at least one test material or component (172, 174, 176, 178). Embodiments of the device include a plurality of different sweat stimulation sites. The Sweat stimulation sites may include one or more sweat stimulant reservoirs (142, 144, 146, 148) configured to deliver a sweat stimulant to the surface of the skin (12). Embodiments may also include at least one electrode (150, 152, 154, 156, 158) for measuring a sweat property or to iontophoretically deliver the sweat stimulant from the reservoir (142, 144, 146, 148). In embodiments, the sweat stimulant is selected from acetylcholine, carbachol, methacholine, bethanechol, muscarine, pilocarpine, oxotremorine, and combinations thereof.

25 Claims, 1 Drawing Sheet

(51) Int. Cl.
  *A61B 5/00* (2006.01)
  *A61N 1/04* (2006.01)
  *A61N 1/30* (2006.01)
(52) U.S. Cl.
  CPC ......... *A61N 1/0448* (2013.01); *A61N 1/0496* (2013.01); *A61N 1/30* (2013.01)
(58) Field of Classification Search
  CPC .. A61N 1/325; A61B 5/0531; A61B 5/14521; A61B 5/4266; A61B 5/6801; A61B 5/6832
  See application file for complete search history.

SKIN PRODUCT SWEAT TESTING DEVICES AND METHODS

BACKGROUND

Skin product testing often involves the influence of sweat on the product performance, such as adhesives, textiles, cosmetics, therapeutics, or any other type of testing of a product or even a skin condition. This is challenging, because inducing sweating in these product tests is typically a global body event and is difficult to control (e.g., using a hot-room, exercise, stress, etc.). This approach is also costly, cumbersome, and can have great variation across each subject or within each subject who participates. Artificial skins have been developed but have difficulty mimicking the full nature of live human skin and its environment.

SUMMARY OF THE INVENTION

Embodiments of the disclosed invention provide devices and methods for digitized skin product sweat testing. Unlike conventional methods, using smart sweat stimulation devices and methods, multiple sweat rates, sweat durations, and control tests can be co-located on a subject.

Described are devices for measuring a sweat property of skin in response to at least one test material or component. Embodiments of the device include a plurality of different sweat stimulation sites. The Sweat stimulation sites may include one or more sweat stimulant reservoirs configured to deliver a sweat stimulant to the surface of the skin. Embodiments may also include at least one electrode for measuring a sweat property or to iontophoretically deliver the sweat stimulant from the reservoir. In embodiments, the sweat stimulant is selected from acetylcholine, carbachol, methacholine, bethanechol, muscarine, pilocarpine, oxotremorine, and combinations thereof. Also described are methods of testing the effectiveness of a material or component during sweat stimulation or the effect of the material or component on sweat production.

The objects and advantages of the disclosed invention will be further appreciated in light of the following detailed descriptions and drawings.

DETAILED DESCRIPTION OF THE INVENTION

One skilled in the art will recognize that the various embodiments may be practiced without one or more of the specific details described herein, or with other replacement and/or additional methods, materials, or components. In other instances, well-known structures, materials, or operations are not shown or described in detail herein to avoid obscuring aspects of various embodiments of the invention. Similarly, for purposes of explanation, specific numbers, materials, and configurations are set forth herein in order to provide a thorough understanding of the invention. Furthermore, it is understood that the various embodiments shown in the figures are illustrative representations and are not necessarily drawn to scale.

Reference throughout this specification to "one embodiment" or "an embodiment" means that a particular feature, structure, material, or characteristic described in connection with the embodiment is included in at least one embodiment of the invention but does not denote that they are present in every embodiment. Thus, the appearances of the phrases "in an embodiment" or "in another embodiment" in various places throughout this specification are not necessarily referring to the same embodiment of the invention. Further, "a component" may be representative of one or more components and, thus, may be used herein to mean "at least one."

Embodiments of the disclosed invention are directed to devices and methods for digitized skin product sweat testing. Examples of products that are tested on skin include adhesives, textiles, cosmetics, and therapeutics. In various embodiments, a skin product may be tested on the skin in relation to one or more varying properties of sweat, such as the duration and rate of sweating. The product may be tested at one or more testing locations on the skin that have different sweat properties. In an embodiment, a control testing location may also be used.

Figure 1A:
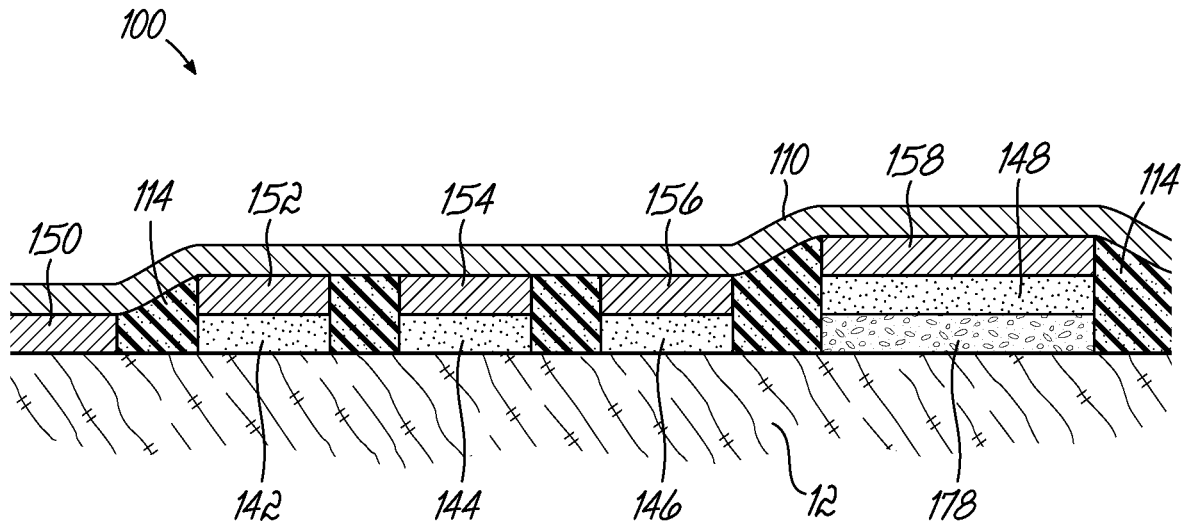
FIG. 1A is a cross-sectional view of a sweat product testing device according to an embodiment of the disclosed invention in a first configuration.

With reference to FIG. 1A, in an embodiment, a device 100 is capable of stimulating a sweating response at one or more testing locations on the skin 12. An embodiment of the disclosed invention includes a plurality of sweat stimulation sites. In an embodiment, the device is also capable of sensing the generated sweat. In the illustrated embodiments of the disclosed invention, the plurality of sweat stimulation sites includes at least one sweat stimulant reservoir 142, 144, 146, 148 containing a sweat stimulant. In embodiments of the disclosed invention, the reservoir is selected from a hydrogel, a paper, a fabric, or a microfluidic pump. An exemplary hydrogel is an agar hydrogel. A hydrogel could also be fumed silica. Examples of a suitable paper include cellulose, nitrocellulose, etc. Examples of a suitable fabric include cotton, polyester, rayon. Examples of a suitable microfluidic pump include for example a connected mechanical syringe pump.

The reservoir 142 includes a surface that contacts the skin to deliver the sweat stimulant. In embodiments of the disclosed invention, the surface of the reservoir 142 that contacts the skin has a surface area sufficient to deliver the sweat stimulant to a desired area of the skin. In an embodiment of the disclosed invention, the surface area of the surface of the reservoir that contacts the skin is in a range from 0.01 $cm^2$ to 50 $cm^2$ or from 0.1 $cm^2$ to 20 $cm^2$ or from 1 $cm^2$ to 10 $cm^2$. In another embodiment of the disclosed invention, the surface area of the surface of the reservoir that contacts the skin is in a range from 0.1 $cm^2$ to 2 $cm^2$. The surface area of the surface of the reservoir may be of a size sufficient to stimulate sweat from a predetermined number of sweat glands. For example, the size of surface area of the surface of the reservoir may be of a size sufficient to stimulate sweat from 1 sweat gland to 1000 sweat glands, or from 1 sweat gland to 10 sweat glands, or from 5 sweat glands to 10 sweat glands, but is not necessarily so limited. The surface of the reservoir 142 that contacts the skin may be of a shape to deliver the sweat stimulant to the desired portion of skin. In embodiments, of the disclosed invention, the shape of the surface of the reservoir 142 that contacts the skin is selected from a square, a rectangular, a circle, an oval, a pentagon, a hexagon, or an octagon, or other suitable shapes.

The sweat stimulant may be delivered via suitable transdermal delivery techniques. In an embodiment, the sweat stimulant is delivered to the skin from the reservoir via diffusion. In another embodiment, the sweat stimulant is iontophoretically delivered.

The device 100 may also include at least one electrode, such as electrodes 150, 152, 154, 156, 158. One or more of the electrodes 150, 152, 154, 156, 158 may be used to iontophoretically deliver a sweat stimulant, to sense a property of the stimulated sweat, or may be used for both functions. For example, the electrode 152 could be a carbon electrode or silver electrode used to drive iontophoresis of a sweat stimulant from the sweat stimulant reservoir 142 into the skin 12 and could also be a skin impedance sensor used to determine a sweat generation rate. For another example, the electrode 150 could be a counter electrode for iontophoresis and/or could measure skin impedance. Other sensors could be added, such as ion-selective sensors, enzymatic sensors, etc. (not shown). One or more materials or components of the device 100 may be coupled to a substrate 110 such as PET, Kapton, or other suitable support structure. The device 100 may also include one or more test materials 178 that need to be tested on skin 12. The exemplary device illustrated in FIG. 1A discloses an electrode 152, 154, 156, and 158 adjacent with each reservoir 142, 144, 146, and 148 on surface of the reservoir opposite the skin contacting surface of the respective reservoir. It will be appreciated that one or more or all, of the reservoirs may be utilized in the device without the presence of an adjacent electrode. This latter configuration may be desired for devices in which the sweat stimulant is delivered to the skin via passive process, such as diffusion and in which the sweat stimulant is not iontophoretically delivered to the skin. Additionally, the embodiments illustrated in FIGS. 1A and 1B have only one electrode in direct contact with the skin, i.e., electrode 150. It will be appreciated the embodiments of the device may include one or more electrodes in direct contact with the skin. For example, in embodiments of the device in which an electrode is not utilized to deliver the sweat stimulant from the reservoir to the surface of the skin, a first electrode and at least a second electrode, such as a counter electrode, can be in direct contact with the skin and may be utilized to sense a condition of the skin, such as skin impedance. It will be appreciated that, as used in herein, the phrase "in direct contact with the skin" may include direct contact as well as contact with the skin through an adhesive or electrolyte gel, but not contact through a sweat stimulant reservoir or test material or component.

The illustrated embodiment includes four distinct testing locations (i.e., the areas of skin adjacent to, or under, the sweat stimulant reservoirs 142, 144, 146, 148. It should be recognized that other embodiments may include one, more than one, or more than four testing locations. Accordingly, the number of electrodes and/or sweat stimulant reservoirs may also vary. In an embodiment, the one or more testing locations on the skin 12 may be fluidically, chemically, mechanically, electrically, or otherwise isolated from each other or from the surrounding skin. For example, the device 100 may include an isolation material 114, such as an adhesive, petroleum jelly, a rubber gasket, an insulator, or other isolating features.

Figure 1B:
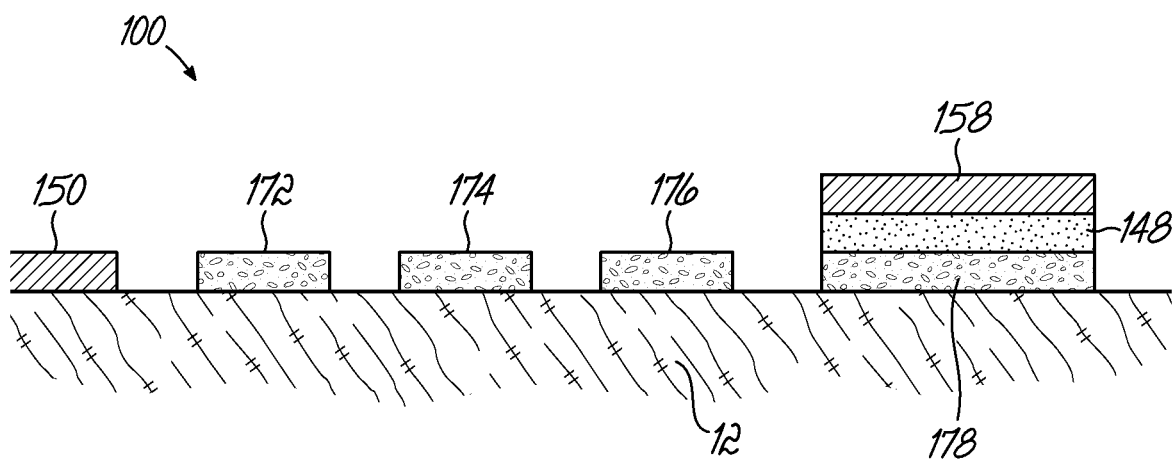
FIG. 1B is a cross-sectional view of a sweat product testing device according to an embodiment of the disclosed invention in a second configuration.

With reference to FIG. 1B, all, or a portion, of the device 100 has been removed and test material(s) or component(s) 172, 174, 176, 178 are being tested in the presence of sweat generation or without the presence of sweat generation, as will be further illustrated in the examples section. The test material or component may be impregnated in a hydrogel, a paper, or a fabric or may be delivered to the surface of the skin via a microfluidic pump. In some embodiments, the test material or component does not need to be delivered to the skin by such a device. For example, an adhesive being tested may not need a structure to deliver the test material to the surface of the skin. In the embodiment illustrated in FIG. 1B, the test material or component 178 is illustrated as being in a stacked configuration with a sweat stimulant reservoir 148 and an electrode 158. I will be appreciated that these components need not be stacked in every embodiment of the invention. For example, the test component or material be situated adjacent to one or both of the sweat stimulant reservoir and the electrode.

In embodiments of the disclosed invention, a sweat stimulation device, such as the exemplary device 100, may produce a sweating response to sweat stimulation using a chemical agent that stimulates sweat, i.e., a sweat stimulant. The sweating response may be prolonged or short and may include a high or low sweat generation rate. A prolonged response to sweat stimulation may be, for example, 24 hours of sweat stimulation based on a single dose of a sweat stimulant that is not readily metabolized by the body. Exemplary sweat stimulants include acetylcholine, carbachol, methacholine, bethanechol, muscarine, pilocarpine, and oxotremorine. As discussed above, these sweat stimulants may be delivered to the surface of the skin by iontophoresis, a microfluidic pump, or by a passive process such as diffusion to stimulate sweat. The sweat response duration, intensity, or both the duration and intensity may be controlled by the choice of sweat stimulant used in the device, the rate of sweat stimulant delivery, the rate at which the subject metabolizes the sweat stimulant, or combinations thereof. Acetylcholine is rapidly metabolized by acetylcholinesterase (AChE), while other sweat stimulants, such as carbachol or methacholine, are metabolized much more slowly (see Table 1 below).

TABLE 1

Activity of Common Cholinomimetic Drugs

| | Receptor Activity | | |
|---|---|---|---|
| Drug | Muscarinic | Nicotinic | AChE Activity |
| Acetylcholine | +++ | +++ | +++ |
| Carbachol | ++ | +++ | − |
| Methacholine | +++ | + | ++ |
| Bethanechol | +++ | − | − |
| Muscarine | +++ | − | − |
| Pilocarpine | ++ | − | − |
| Oxotremorine | ++ | − | − |

In order to facilitate a more complete understanding of the embodiments of the invention, the following non-limiting examples are provided.

EXAMPLE 1

A skin adhesive product is to be tested for its adhesive strength and longevity in the presence of sweat. A device, such as device 100, includes components 172, 174, 176, which all include the product to be tested. The device is placed on skin to test each of the products 172, 174, 176 against different durations of sweating. A prolonged response of sweating is generated where the product 172 experiences a sweat generation rate of greater than 0.5 nL/min/gland for 2 hours and the product 174 experiences a sweat generation rate of greater than 0.5 nL/min/gland for 6 hours. The product 176 is used as a control and experiences no sweating (i.e., the sweat glands under the product 176 undergo no stimulation). To produce the varied prolonged responses for the products 172, 174, the dose of sweat stimulant such as carbachol delivered to the skin may be controlled (e.g., charge/second and/or duration).

When sweat stimulation is applied using the configuration of the device 100 of FIG. 1A, one or more of the electrodes, such as electrode 152, may also sense sweat generation rate by measurement of skin impedance. When the device configuration of the device 100 of FIG. 1B is used, the sweat generation rate could be quantified by measuring gravimetrically with placing of weighed filter paper (not shown) above each product such as product 172.

When the device configuration of FIG. 1A or 1B is used, alternate stimulants (e.g., shorter or longer acting) and doses of sweat stimulation can be applied in real time by electrode 158 and sweat stimulant reservoir 148. For example, repeated short sweat stimulation events can be achieved by dosing of acetylcholine. Sweat stimulant reservoir 148 and electrode 158 could be removed after each stimulation, or could remain on such a device, whichever is most suitable for the desired testing parameters. If product 178 were an adhesive hydrogel, for example, it can easily allow the sweat stimulant from the sweat stimulant reservoir 148 to pass through the adhesive product 178 to the skin 12. Alternately, the product 178 could be discontinuous (e.g., have holes or spaces in it) to allow indirect sweat stimulation through such holes or spaces and spreading of the sweat response to all areas under the product 178 by means of diffusion of the sweat stimulant or by means of sudomotor axon reflex sweating.

This same Example 1 could be used to test a product against a variable of sweat generation rate rather than the variable of duration of sweating. In an embodiment, sweat may be stimulated such that the sweat generation rates in the areas adjacent to the different products differ (e.g., sweat generation rates of 0.5 nL/min/gland, 2 nL/min/gland, and 5 nL/min/gland). For example, one could wait an hour or more after a sweat stimulant is delivered for the sweat generation rates to become stable, and then test the products against the different sweat generation rates all on the same location, such as the back or under the shaved axilla, of a test subject.

EXAMPLE 2

A skin antiperspirant product is to be tested for its efficacy in stopping or slowing perspiration over time. Sweat stimulants that generate sweating responses of different durations may be applied to distinct areas of the skin to test the antiperspirant product over the different durations. With reference to FIG. 1A, the sweat stimulant reservoirs 142, 144, 146 could contain acetylcholine, pilocarpine, and carbachol, respectively. A short (e.g., 1 minute) but equal dose (0.5 mA/cm$^2$) of the acetylcholine, pilocarpine, and carbachol could be delivered by the electrodes 152, 154, 156, respectively.

After stimulation was applied with FIG. 1A, the device 100 could be quickly removed and antiperspirant product applied within 1 minute to 2 more minutes. Within 5 minutes, generated sweat would appear. Due to the different stimulants used, the areas of the skin adjacent to the reservoirs 142, 144, 146 would generate stimulated sweating for different durations. The sweating response durations of the acetylcholine, pilocarpine, and carbachol could be 5 minutes to 7 minutes, 60 minutes to 90 minutes, and 6 hours to 12 hours, respectively. The duration of efficacy for the antiperspirant could therefore be tested and assessed using skin impedance, gravimetric, optical, or other suitable sensing means. Additional sites could be tested as control sites as well (i.e., no sweating induced).

EXAMPLE 3

Experiments are conducted similar to that of the previous example, but no skin product is tested, rather the natural state or health or disease of skin is tested. For example, eczema, a rash, skin hydration, microflora, or other factors on skin and skin health could be tested as a function of sweat generation rate. Measures could include photographs, spectrometry, analytical chemistry, or other known methods for analyzing the status of skin.

While specific embodiments have been described in considerable detail to illustrate the disclosed invention, the description is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A device for measuring a sweat property comprising one or more sweat stimulant reservoirs configured to deliver a sweat stimulant to the surface of the skin, at least one electrode for measuring a sweat property, and at least one test material or component;
   wherein the at least one test material or component is impregnated into a secondary material.

2. The device of claim 1, wherein the sweat stimulant is selected from at least one member from the group consisting of acetylcholine, carbachol, methacholine, bethanechol, muscarine, pilocarpine, oxotremorine, and combinations thereof.

3. The device of claim 1, wherein the sweat property is skin impedance.

4. The device of claim 1, wherein the at least one electrode is further configured to iontophoretically deliver the sweat stimulant to the surface of the skin from at least one reservoir.

5. The device of claim 1 wherein the secondary material is at least one of a hydrogel, a paper, or a fabric configured to deliver the test material or component to the surface of the skin.

6. The device of claim 1, wherein the at least one electrode is in direct contact with the skin.

7. A method of evaluating the effect of a test material or component on sweat production utilizing the device of claim 1.

8. A device for measuring a sweat property comprising one or more sweat stimulant reservoirs configured to deliver a sweat stimulant to the surface of the skin, at least one electrode for measuring a sweat property, and at least one test material or component;
   wherein the at least one test material or component is stored in a microfluidic pump configured to deliver the test material or component to the surface of the skin.

9. The device of claim 8, wherein the sweat stimulant is selected from at least one member from the group consisting of acetylcholine, carbachol, methacholine, bethanechol, muscarine, pilocarpine, oxotremorine, and combinations thereof.

10. The device of claim 8, wherein the sweat property is skin impedance.

11. The device of claim 8, wherein the at least one electrode is further configured to iontophoretically deliver the sweat stimulant to the surface of the skin from at least one reservoir.

12. The device of claim 8, wherein the at least one electrode is in direct contact with the skin.

13. A method of evaluating the effect of a test material or component on sweat production utilizing the device of claim 8.

14. A device for measuring a sweat property comprising one or more sweat stimulant reservoirs configured to deliver a sweat stimulant to the surface of the skin, at least one electrode for measuring a sweat property, and at least one test material or component;
wherein the at least one test material or component is positioned between the skin and the sweat stimulant reservoir.

15. The device of claim 14, wherein the sweat stimulant is selected from at least one member from the group consisting of acetylcholine, carbachol, methacholine, bethanechol, muscarine, pilocarpine, oxotremorine, and combinations thereof.

16. The device of claim 14, wherein the sweat property is skin impedance.

17. The device of claim 14, wherein the at least one electrode is further configured to iontophoretically deliver the sweat stimulant to the surface of the skin from at least one reservoir.

18. The device of claim 14, wherein the at least one electrode is in direct contact with the skin.

19. A method of evaluating the effect of a test material or component on sweat production utilizing the device of claim 14.

20. A device for measuring a sweat property comprising one or more sweat stimulant reservoirs configured to deliver a sweat stimulant to the surface of the skin, at least one electrode for measuring a sweat property, and at least one test material or component;
wherein the at least one test material or component and the sweat stimulant reservoir are positioned between the skin and the at least one electrode.

21. The device of claim 20, wherein the sweat stimulant is selected from at least one member from the group consisting of acetylcholine, carbachol, methacholine, bethanechol, muscarine, pilocarpine, oxotremorine, and combinations thereof.

22. The device of claim 20, wherein the sweat property is skin impedance.

23. The device of claim 20, wherein the at least one electrode is further configured to iontophoretically deliver the sweat stimulant to the surface of the skin from at least one reservoir.

24. The device of claim 20, wherein the at least one electrode is in direct contact with the skin.

25. A method of evaluating the effect of a test material or component on sweat production utilizing the device of claim 20.

* * * * *